(12) United States Patent
Kendall

(10) Patent No.: US 7,909,793 B2
(45) Date of Patent: Mar. 22, 2011

(54) SILENCING DEVICE AND METHOD FOR NEEDLELESS SYRINGE

(75) Inventor: Mark Anthony Fernance Kendall, Oxford (GB)

(73) Assignee: Powderject Research Limited, Oxford (GB)

( * ) Notice: Subject to any disclaimer, the term of this patent is extended or adjusted under 35 U.S.C. 154(b) by 2051 days.

(21) Appl. No.: 10/484,742

(22) PCT Filed: Jul. 25, 2002

(86) PCT No.: PCT/GB02/03412
§ 371 (c)(1),
(2), (4) Date: Mar. 12, 2004

(87) PCT Pub. No.: WO03/011380
PCT Pub. Date: Feb. 13, 2003

(65) Prior Publication Data
US 2005/0010168 A1    Jan. 13, 2005

(30) Foreign Application Priority Data

Jul. 26, 2001  (GB) .................................. 0118266.6

(51) Int. Cl.
*A61M 5/30* (2006.01)
(52) U.S. Cl. ......................................... 604/68; 604/207
(58) Field of Classification Search ............... 128/200.11–200.29; 604/68–72, 604/207–211
See application file for complete search history.

(56) References Cited

U.S. PATENT DOCUMENTS

| | | | |
|---|---|---|---|
| 3,308,818 A | 3/1967 | Rutkowski | |
| 5,238,003 A * | 8/1993 | Baidwan et al. | 600/578 |
| 5,503,627 A * | 4/1996 | McKinnon et al. | 604/72 |
| 5,865,803 A * | 2/1999 | Major | 604/122 |
| 6,004,286 A | 12/1999 | Bellhouse et al. | |
| 6,004,287 A | 12/1999 | Loomis et al. | |
| 6,010,478 A * | 1/2000 | Bellhouse et al. | 604/70 |
| 6,475,181 B1 * | 11/2002 | Potter et al. | 604/68 |
| 6,592,545 B1 * | 7/2003 | Bellhouse et al. | 604/69 |
| 7,060,048 B1 * | 6/2006 | Nat et al. | 604/70 |
| 7,207,967 B1 * | 4/2007 | Bellhouse et al. | 604/70 |
| 7,320,677 B2 * | 1/2008 | Brouillette | 604/68 |
| 2002/0004641 A1 * | 1/2002 | Bellhouse et al. | 604/68 |

FOREIGN PATENT DOCUMENTS

EP    1 090 651 B1    4/2001
(Continued)

*Primary Examiner* — Nicholas D Lucchesi
*Assistant Examiner* — Gerald Landry, II
(74) *Attorney, Agent, or Firm* — Foley & Lardner LLP

(57) ABSTRACT

The invention provides a silencer and silencing method which ensures adequate silencing with no deleterious increase in back pressure (which creates a lift-off force) or decrease in device performance. Pressurized gas is supplied to a driver chamber by a bleed-hole having an effective bleed-hole area and, during use of the device for particle delivery, gas is vented to the atmosphere via a silencer having an effective venting area. The bleed-hole area and venting area are chosen to ensure that the mass flow rate of gas through the effective venting area is substantially equal to or greater than the mass flow rate of gas through the effective bleed-hole area. This ensures that there is no build up of gas in the silencer device which tends to increase back pressure and hence lift-off force. Preferred embodiments of the device comprise a silencer having a large volume and a small particle exit opening. Further, there is disclosed an embodiment using one or more transfer ducts to assist particle mixing.

29 Claims, 9 Drawing Sheets

FOREIGN PATENT DOCUMENTS

Figure 1:
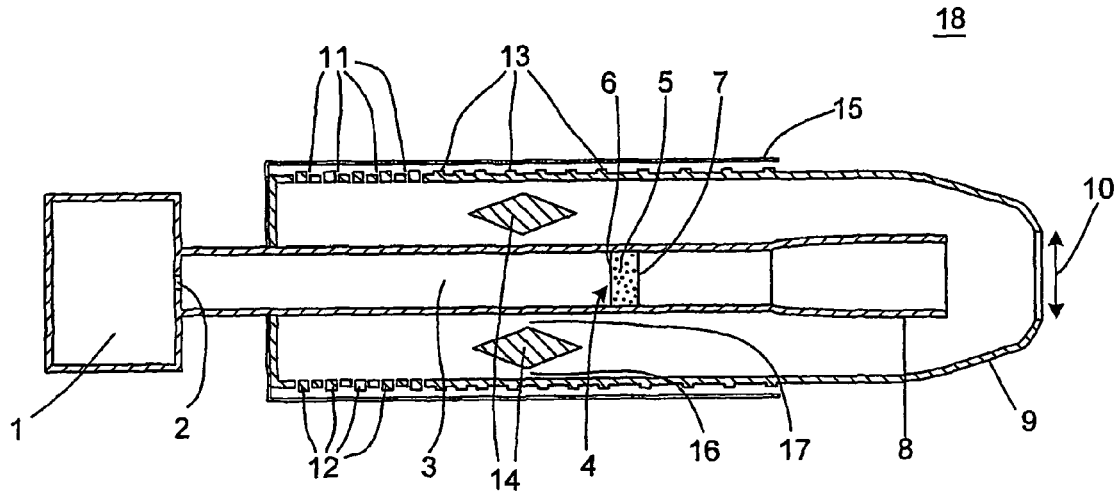

| | | |
|---|---|---|
| FR | 873453 | 7/1942 |
| WO | WO 94/24263 | 10/1994 |
| WO | WO 96/04947 | 2/1996 |
| WO | WO 96/12513 | 5/1996 |
| WO | WO 99/01168 | 1/1999 |
| WO | WO 99/01169 A1 | 1/1999 |
| WO | WO 00/62846 | 10/2000 |
| WO | WO 01/05455 | 1/2001 |

* cited by examiner

SECTION A-A

Values show velocity in M/S

SILENCING DEVICE AND METHOD FOR NEEDLELESS SYRINGE

The present invention relates generally to the field of particle delivery and more particularly to needleless syringes which accelerate particles in a gas stream so as to deliver them into a target (such as the tissue of a subject).

WO 94/24263 discloses a needleless syringe for the injection of particles. Upon activation of the device, pressurised gas is supplied to a small rupture chamber in which there is located a particle cassette comprised of particles sandwiched between two rupturable membranes. Once pressure in the small rupture chamber has reached a certain value, the membranes rupture and gas continues to be supplied such that the particles are accelerated down a nozzle and into the target. After the particles have impacted the target, the gas used for accelerating the particles is routed past a series of baffles, to break down the reflected shockwave and provide a silencing effect, before being vented to the atmosphere.

In a device of this type, the chamber in which gas builds up initially is of a small volume and gas flowing into the chamber after rupture of the membranes is important in accelerating the particles. This fact is confirmed by WO 99/01168 in which a device having a large area valve is provided so that gas can continue to flow from the gas reservoir and down the nozzle after rupture of the membranes. This document suggests the same silencing mechanism as WO 94/24263.

WO 01/05455 discloses a needleless syringe device in which substantially all of the particles are delivered in a quasi-steady gas flow which is established after the passage of a starting process. This allows the particles to be reliably and repeatedly delivered.

In contrast to WO 94/24263 and WO 99/01168, WO 01/05455 proposes the use of a bleed-hole which limits the flow of gas from the reservoir to the chamber behind a closure means once the closure means has burst. In fact, substantially all of the particles are accelerated by the gas which builds up behind the closure means prior to bursting and the gas which flows from the reservoir after bursting has a negligible effect on accelerating the particles.

It has been found that the shockwave emitted by the device of WO 01/05455 can cause a loud noise to emanate from the device in use. It is desirable for this noise to be kept as small as possible so as to avoid alarming users of the device. At present, no silencer has been proposed that is suitable for use with a syringe of the form disclosed in WO 01/05455.

An attempt to apply the silencing teaching of WO 94/24263 or WO 99/01168 to the syringe at WO 01/05455 has not proved to be fruitful since the earlier silencer confines pressurised gas to an area near the target plane which creates a substantial lift-off force tending to move the device away from contact with the target. This is undesirable because the device should stay in contact with the target during injection if proper injection is to be ensured and because lift-off of the device releases gas allowing sound to escape, increasing noise. Any lift-off also allows particles to escape to the atmosphere instead of impacting the target. The high pressure near the target plane also impedes particle flow resulting in lower particle impact velocities, reducing the performance of the device.

Thus, there is a need for a needleless syringe having the improved operation of WO 01/05455 but which is quieter in operation, the silencing not affecting the performance of the device in delivering particles. The teaching of the present invention may be advantageously applied to other types of needleless syringes as well.

Accordingly, the present invention provides a needleless syringe device comprising:
an energy source;
at least one bleed-hole, said bleed-hole(s) having an effective bleed-hole area for the passage therethrough of pressurised gas from the energy source to a driver chamber to entrain particles and accelerate them into a target; and
a silencer for receiving said gas from said driver chamber and for venting that gas to the surroundings of the silencer through at least one silencer vent opening, said vent opening(s) having an effective venting area;
wherein said effective bleed-hole area and said effective venting area are such that, during use of the device for particle delivery, the mass flow rate of gas through aid effective venting area is substantially equal to or greater than the mass flow rate of gas through said effective bleed-hole area.

The fact that the mass flow rate of gas through the venting area is equal to or greater than the mass flow rate of gas through the bleed-hole area ensures that as much or more gas leaves the device during operation as is provided by the energy source. This ensures that the pressure inside the silencing shroud of the device does not increase as the device is operated and thus serves to limit a deleterious build up in back pressure which can result in the device lifting off from the target plane. Preferably, the venting area and bleed-hole areas are sized to ensure that the mass flow rate through the venting area is greater than the mass flow rate through the bleed-hole area during use such that, after the initial expansion of gas from the driver chamber to the shroud, the pressure actually reduces inside the shroud during use. Preferably, the venting area is small enough to provide adequate silencing and large enough to ensure that pressure does not build up in the device during use.

Preferably, the energy source is a reservoir of pressurised gas, such as helium or nitrogen.

To ensure that the mass flow rate of gas through the venting area is greater than the mass flow rate of gas through the bleed-hole area, the ratio of venting area to bleed-hole area should be equal to or greater than a constant, k, given by the following expression:

$$k = \left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S}$$

wherein $\gamma_1$ is the ratio of specific heats for the gas in the reservoir, $R_1$ is the gas constant for the gas in the energy source (reservoir), $\gamma_2$ is the ratio of specific heats for the gas in the surroundings, $R_2$ is the gas constant for the gas in the surroundings, $P_0$ is the pressure in the energy source after gas has been received by said silencer and $P_S$ is the pressure in the silencer after gas has been received by said silencer.

More preferably, the ratio of venting area to bleed-hole area should be greater than or equal to 1.2 k to ensure a sufficient decay of pressure within the silencer. To ensure adequate silencing, the ratio of venting area to bleed-hole area should preferably be less than 20 k, more preferably less than 10 k, still more preferably less than 5 k.

In a preferred embodiment, the silencer comprises a shroud having a predetermined volume for containing the gas received from the driver chamber prior to venting it.

The volume of the shroud, the volume of the driver chamber and the size of the exit opening should preferably be chosen such that when the closure is opened and gas flows from the driver chamber to the shroud, the resulting equalisation in pressure results in a lift-off force on the device of less than 20N, more preferably less than 15N.

In this specification the term 'closure' includes both 'closure means' and 'closure member'.

Preferably, the particles are delivered through a particle exit opening in the shroud which is pressed against the target during use.

Preferably, said at least one silencer vent opening is formed by at least one hole provided in the shroud and this at least one hole is preferably located in the upstream end of the device so that the gas must travel substantially the length of the device before it can be vented through said at least on hole.

To provide further passages for the gas, a cover may be attached to the device to create an annular channel for the passage of gas from the shroud to the surroundings. This annular channel may comprise a plurality of baffles which interact with the gas flow vented out of the shroud and attenuate any shockwaves in the gas flow. Alternatively or additionally, baffles or the like may be included inside the shroud volume itself.

Preferably, the particle-containing gas which flows from the driver chamber is expanded by a nozzle connected to the driver chamber and this nozzle is preferably substantially correctly expanded, although it need not be to obtain adequate performance.

To further limit the lift-off force experienced during use of the device, the particle exit opening in the shroud should be preferably no more than 100% larger than the exit area of the nozzle. The particle exit opening should also be axially spaced from the nozzle exit so that a path for the venting of gas is provided.

The present invention also provides a method of silencing a particle-accelerating gas flow, the method comprising:
(a) supplying pressurised gas through a bleed-hole at a first mass flow rate;
(b) accelerating particles with said pressurised gas so supplied such that said particles will achieve a velocity sufficient to penetrate into a target;
(c) receiving said gas in a silencer and venting said received gas to the surroundings through at least one silencer vent opening at a second mass flow rate;
wherein said second mass flow rate is substantially equal to or greater than said first mass flow rate.

The present invention furthermore provides a needleless syringe device comprising:
an energy source;
at least one bleed-hole, said bleed-hole(s) having an effective bleed-hole area for the passage therethrough of pressurised gas from the energy source to a driver chamber;
a first closure located at a downstream end of said driver chamber;
a second closure located downstream of said first closure to create a particle retention chamber therebetween; and
at least one transfer duct providing a gas flow path between said driver chamber and said particle retention chamber,
wherein said effective bleed-hole area and the minimum area of said transfer duct(s) are selected such that, in use, said first closure opens before said second closure and said second closure opens at least 2 ms after gas starts to flow through said transfer duct(s).

Correct selection of the bleed-hole size and transfer duct size allows the correct sequence of closure opening to be effected in use, avoiding problems associated with the downstream closure opening first or with both closures opening before the particles have properly mixed with the gas provided by the transfer duct(s). More preferably, particle mixing times of at least 3.5 ms or 5 ms are provided. In a preferred embodiment, the first and second closure are rupturable membranes which open by rupturing.

There is also provided a method of uniformly accelerating particles in a gas flow, the method comprising:
(a) supplying pressurised gas to a driver chamber,
(b) supplying some of said pressurised gas in said driver chamber to a particle retention chamber downstream of said driver chamber to thereby fluidize said particles;
(c) opening an upstream closure of said particle retention chamber;
(d) opening a downstream closure of said particle retention chamber;
wherein said downstream closure opens at least 2 ms after said supplying step (b) starts.

There is furthermore provided a particle retention assembly comprising:
a particle retention chamber bounded by an upstream closure and a downstream closure;
at least one duct providing a gas flow path into said chamber;
wherein said duct is constructed to supply gas to said particle retention chamber from a substantially annular space around said particle retention chamber.

The annular space around the particle retention chamber allows, in a simple and convenient manner, one or more transfer ducts to be supplied with gas. The annular space means that the transfer ducts can be located virtually anywhere on the inside surface of the particle retention chamber. The annular space used to supply the gas is also a particularly convenient shape from the point of view of manufacturing and it will be seen that a particle retention assembly according to this aspect of the invention can be manufactured from only three separate cassette parts and three membranes.

There is furthermore provided a particle retention assembly comprising:
a particle retention chamber bounded by an upstream closure and a downstream closure;
a first duct providing a first gas flow path into said chamber,
wherein said first duct is arranged, in use, to create a first swirl of gas in said particle retention chamber.

The swirl of gas in the particle retention chamber is particularly efficient in fluidizing the particles so that they form a "cloud" which substantially spans the particle retention chamber, resulting in a more uniform particle distribution and velocity and, hence, penetration profile.

Preferably, there are at least two ducts which, in use, create at least two swirls of gas in the particle retention chamber, these swirls of gas being preferably directed in substantially different directions. The swirls of gas may advantageously be created by jets emanating from the transfer ducts, these jets being at least momentarily sonic or supersonic during use. To aid particle fluidization, the ducts can be off-set from one another in the direction of gas flow, and circumferentially.

The annular space around the particle retention chamber is preferably connected to a region upstream of the upstream closure by means of a series of circumferential ports.

A further closure provided to ensure the sterility of particle retention assembly may be provided.

There is also provided a method of fluidizing particles in a particle retention chamber, the method comprising:
supplying pressurised gas to an annular space around said particle retention chamber;
supplying said gas to said chamber using at least one transfer duct so as to fluidize any particles located in said particle retention chamber.

There is furthermore provided a method of fluidizing particles in a particle retention chamber, the method comprising:

supplying pressurised gas to a first duct fluidly connected to said particle retention chamber;

creating a first swirl of gas in said particle retention chamber so as to fluidize any particles located in said particle retention chamber.

Embodiments of the invention will now be further described, by way of example only, with reference to the accompanying schematic drawings, in which:—

FIG. 1 is an axi-symmetric cross-sectional view of a needleless syringe device having a silencer according to the present invention;

FIG. 2 is a first side cross-sectional view of a practical embodiment of the present invention;

FIG. 3 is a second side cross-sectional view of the FIG. 2 embodiment of the present invention, viewed along the line X-X in FIG. 2;

FIG. 4 is a graph of pressure in the shroud versus time for three different bleed-hole sizes;

FIG. 5 is a cross-sectional view of part of a needleless syringe showing a transfer duct linking the driver chamber and particle retention chamber;

FIG. 6 is a graph showing pressure in the driver chamber and particle retention chamber for the case when the bleed-hole is too small;

FIG. 7 is a graph showing pressure in the driver chamber and particle retention chamber for the case when the bleed-hole is too large;

FIG. 8 is a graph showing pressure in the driver chamber and particle retention chamber for the case when the bleed-hole is correctly sized;

FIG. 9 is a drawing of a particle retention assembly (also referred to as a particle cassette) according to the present invention;

FIGS. 10*a* to 10*d* are drawings showing stages in the flow of gas around the particle retention assembly during which particles are fluidized and entrained in a gas flow;

FIG. 11 is a cross-sectional view of a second cassette part, the second cassette part being a part of the particle retention assembly of the present invention;

FIG. 12 is a cross-sectional view of a first cassette part, the first cassette part being part of the particle retention assembly of the present invention;

FIG. 13 is a cross-sectional view along the line A-A shown in FIG. 12;

FIG. 14 is a cross-sectional view of a third cassette part, the third cassette part being part of the particle retention assembly of the present invention;

FIG. 15 is a cross-sectional view of an assembled particle retention assembly according to the present invention;

FIG. 16 shows two partially cut away perspective views of an embodiment of the particle retention assembly according to the present invention;

FIG. 17 shows the result of a computational fluid dynamic calculation showing the velocity of gas inside the particle retention chamber during use; and FIG. 18 is a close up view of the velocity distribution of gas in a plane bisecting a transfer duct and being perpendicular to the longitudinal direction of the particle retention assembly.

FIG. 1 of the accompanying drawings schematically illustrates the silencing concept of the present invention. The needleless syringe components comprising the reservoir (1), the bleed-hole (2), the driver chamber (3), the closure (4) and the nozzle (8) can be constructed and arranged substantially as is disclosed in WO 01/05455, the disclosure of which is incorporated herein by reference.

In FIG. 1, an energy source is represented by a reservoir (1) initially filled with pressurized gas, such as helium. The reservoir is connected to a driver chamber (3) by a bleed-hole (2) and a valve (not shown). Upon opening of the valve, gas flows from the reservoir (1) to the driver chamber (3) via the bleed-hole (2) because the gas pressure in the reservoir (1) is initially higher than the gas pressure in the driver chamber (3). The driver chamber may initially contain air because this is the most convenient gas, although it can be made initially to contain other gases, e.g. helium. A closure (4) defines the downstream end of the driver chamber (3) and serves initially to create a build-up of gas behind it. In FIG. 1, the closure is represented as a particle cassette of the type disclosed in WO 94/24263 in which particles (5) are sandwiched between two rupturable membranes (6, 7). The cassette may however take other forms, for example it may be a membraneless cassette.

FIG. 1 also shows a silencer shroud (9) encapsulating the syringe and having an exit opening (10) for the passage therethrough, to a target (not shown), of particles and also having a plurality of openings (11) for the venting of gas to atmosphere.

Upon actuation of the valve, gas flows from the reservoir (1) into the driver chamber (3) where it is contained by the closure (4). Gas continues to flow from the reservoir (1) to the driver chamber (3) until a certain predetermined pressure is established in the driver chamber (3), this pressure being the pressure required to open the closure (4). In the illustrated embodiment, this pressure corresponds to the pressure at which the diaphragms (6, 7) rupture. Upon rupturing of the diaphragms (or, more generally, upon opening of the closure) a pressure discontinuity is created in the device such that a shockwave travels downstream towards a nozzle (8). The shockwave is a front delimiting gas at a high pressure from the gas at atmospheric pressure initially in the nozzle. The shockwave travels down the nozzle and impacts the target plane adjacent the exit opening (10), at which point it is reflected so that a portion of it travels in the annular space internally of the silencing shroud (9) and externally of the nozzle (8). At the same time, the gas which flows from the driver chamber behind the shockwave entrains the particles (5) such that they pass along the nozzle and through the exit opening (10) to impact the target plane at a velocity sufficient to penetrate it.

The silencer shroud (9) is configured to encapsulate a predetermined volume of gas $V_S$. This volume is defined as all of the volume inside the silencer shroud, including that of the driver chamber and the nozzle. Once the shockwave has passed out of the silencer shroud through the plurality of holes (11) included in the shroud, the gas in initially in the driver chamber has expanded into the silencer shroud and the resulting pressure inside the silencer shroud becomes generally constant and is given by the following equation:

$$P_S = \frac{(P_D - P_{S0}) \cdot V_D}{V_S} + P_{S0}$$

where $P_S$ is the pressure in the silencer shroud after pressure equalisation, $P_D$ is the pressure in the driver chamber just prior to opening of the closure (4), $P_{S0}$ is the pressure in the silencer initially, $V_D$ is the volume of the driver chamber (ie that volume between the bleed-hole (2) and the closure (4)) and $V_S$ is the volume of the shroud (which incorporates the volume of the driver chamber and the nozzle). If the mass flow rate through the venting area is larger than that through the bleed hole, this pressure then decays with time as gas is vented from the silencer.

The above equation assumes an isothermal expansion in which the temperature of the gas before expanding is the same as after expanding. Thus, in the usual case where the silencer shroud is initially at atmospheric pressure ($P_{SO}$=100 kPa) and for a typical driver chamber volume $V_D$ of 4.5 ml, silencer shroud volume $V_S$ of 50 ml and driver pressure $P_D$ of 1570 kPa, the pressure $P_S$ in the silencer shroud would settle down to around 232 kPa once the shockwave has passed. It is this pressure which determines the initial lift-off force that a user experiences upon activating the device. In particular, the lift-off force is equal to the pressure ($P_S$–$P_0$) multiplied by the area of the exit opening (10) (i.e. the area over which the differential pressure acts, $P_0$ being the pressure in the surroundings, typically 100 kPa). A typical exit opening area is 100 mm$^2$ which results in a lift-off force of approximately 13.2 N.

Figure 4:
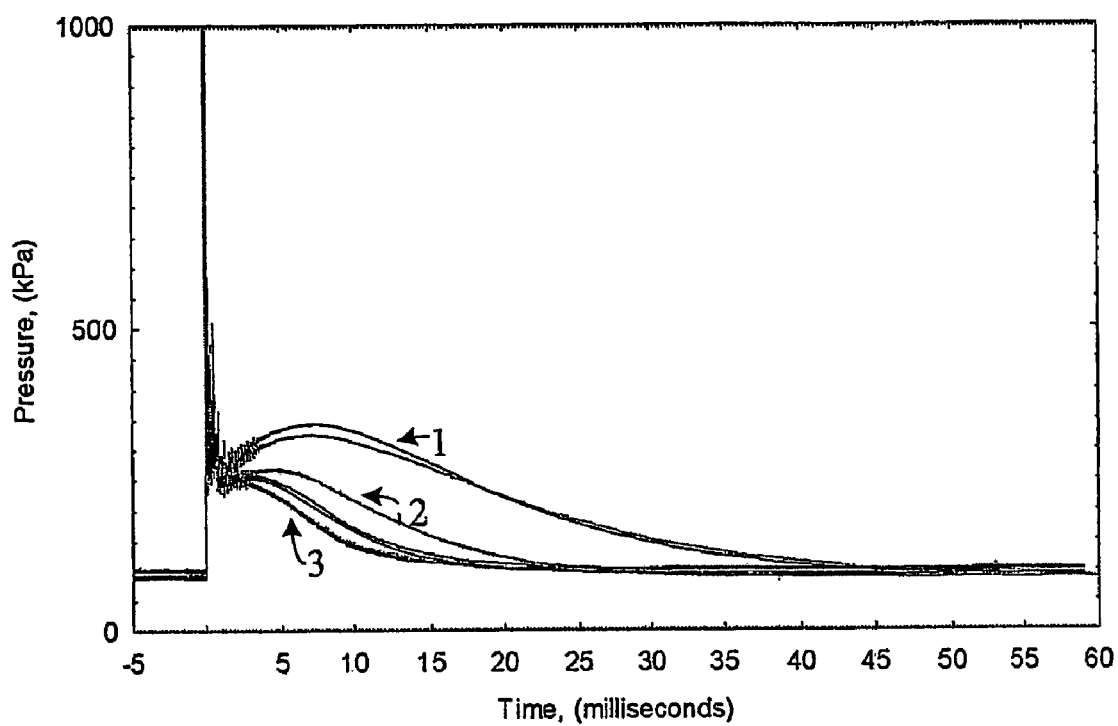

FIG. 4 illustrates the experimentally obtained effect of varying the size of the bleed-hole in relation to the venting area of the silencer, other parameters such as exit plane area, shroud volume etc. remaining constant. In the experiment the venting area was kept constant and the size of the bleed hole was varied. The graph shows the pressure inside the shroud plotted against time.

In all cases, there is a large initial sudden increase in pressure as the shock wave passes through the device. The pressure decays very quickly to a value of about 260 kPa and then follows a decay curve that is determined by the relationship between bleed hole size and effective venting area. The references hereinafter to peak shroud pressure refer to the maximum shroud pressure attained in the decay curve, i.e. after the large initial pressure increase shown in FIG. 4.

The line numbered "1" is the case where the effective venting area/bleed hole ratio is too low. This results in an absolute peak shroud pressure of about 340 kPa after 7.5 ms which is large enough to cause an unacceptable lift-off force. A peak sound level of 102-108 dB at 300 mm from the device was measured.

The line numbered "2" is the case where the effective venting area/bleed hole ratio has been increased. This results in a peak shroud pressure of about 270 kPa after 4.25 ms. The measured peak sound level was increased to 106-110 dB at 300 mm from the device.

The line numbered "3" is the case where the effective venting area/bleed hole ratio is increased further. This results in a shroud pressure which has its peak as soon as the shock wave has passed and decays. A peak sound level of 115-118 dB at 300 mm from the device was measured.

Thus, the ratio of curve "1" is unacceptable but that of curves "2" and "3" are acceptable since the pressure does not increase substantially as a result of higher mass flow rate through the bleed hole than through the effective venting area. Curve "2" is more desirable than curve "3" since the peak lift-off force is about the same as for curve "3" but the silencing effect is greater, there being a 8-9 dB difference in sound levels obtained.

It will be appreciated that one preferable way of reducing the lift-off force is to ensure that the volume of the silencer shroud ($V_S$) is as large as possible so as to reduce the value of $P_S$ (see equation above). Another preferable way to reduce the lift-off force is to make the area of the exit opening (10) as small as possible so that the pressure $P_S$ acts over a smaller area, creating a lower force.

The noise that is experienced upon actuation of the device is mainly due to the shockwave initiated from the sudden opening of closure (4) which is reflected from the target and exits the device through the venting area. It has been found that passing such a shockwave through a restriction, thereby breaking it down into compression waves, creates a lower level of audible sound. Thus, the effective silencer restriction presented to the shockwave (and subsequent flow) is an important device parameter. The effective silencer restriction is defined as the smallest area through which the shockwave travels on its way from the target plane to the surroundings. In FIG. 1, three main restrictions are shown, either one of which, two of which, or even all of which (if all are of equal size), may represent the effective silencer restriction. The first restriction encountered by the reflected shockwave on its passage from the opening (10) to the surroundings (18) is that due to the member (14) which is provided in the annular space of the shroud (9). This member (14) comprises an annular ring of generally diamond-shaped cross-section which is suspended in the device by attachment to one or more of the wall of the shroud (9) and the wall of the driver chamber (3) via one or more radial arms (not shown). As can be seen from FIG. 1, the presence of the member (14) causes a restriction in the path of the shockwave so that the shockwave is forced to pass through two concentric generally annular passages labelled (16) and (17) in FIG. 1. The sum of the area of these two passages is equal to the area through which the shockwave is confined to travel. This is the first restriction.

The second restriction is presented by the plurality of holes (11) formed in the outer wall of the shroud (9), the sum of the areas of each of the holes is equal to the area that the shockwave must pass through.

The third restriction is created by the cover member (15) placed around the shroud (9) and the series of baffles (12, 13) on the outer surface of the shroud (they may equally be provided on the inner surface of the cover member (15)). The annular passage created between the cover member and the shroud has an area through which the shockwave must pass. The third restriction is the part of this annular passage presenting the smallest area to the shockwave.

The smallest of the first second and third areas described above will be equal to the effective venting area of the silencer and will determine the maximum mass flow rate that can pass through the silencer and into the surroundings. The smaller this area, the smaller the mass flow rate of gas that can pass into the surroundings but also the more noise attenuation occurs through the breakdown of the primary shock. In the limit of a restriction have an area of zero mm$^2$ (i.e. the shroud is completely closed), no gas can pass into the surroundings and the device should in theory be silent at a result.

Since the effective venting area affects the mass flow rate that can pass into the surroundings, there is a relationship between this area and the pressure that builds up in the shroud (9) during use. In particular, if the maximum mass flow rate that can pass out of the silencer (comprising the shroud (9), the holes (11), the baffles (12, 13) and the member (14)) is less than the mass flow rate being supplied by the reservoir (1) through the bleed-hole (2) then it will be seen that pressure builds up in the device once the shockwave has passed, serving to increase the lift-off force, which is undesirable. Thus, in accordance with the present invention, the effective venting area of the silencer should be such that the mass flow rate out of the silencer is equal to or greater than the mass flow rate of gas through the bleed-hole (2) once the closure has opened and the shockwave has passed out of the device. To achieve this condition with the schematically shown device (i.e. one in which the energy source is a reservoir of pressurised gas), the following equation gives the relative size of the bleed-hole area and venting area:

$$\frac{\text{venting area}}{\text{bleed-hole area}} > \left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S}$$

wherein $\gamma_1$ is the ratio of specific heats for the gas in the reservoir (1), $R_1$ is the gas constant for the gas in the reservoir (1), $\gamma_2$ is the ratio of specific heats for the gas in the surroundings (18), $R_2$ is the gas constant for the gas in the surroundings (18), $P_0$ is the pressure in the energy source (1) after gas has been received by said silencer (9) and $P_S$ is the pressure in the silencer (9) after gas has been received by said silencer (9).

Since it is beneficial to have as small an effective venting area as is possible (to maximise the silencing effect), it is necessary to have a small bleed-hole (2) to ensure that the mass flow rate through the bleed-hole does not exceed the mass flow rate through the silencer. There is a limit, however, to the smallest size that the bleed-hole can be since the bleed-hole must be large enough to allow the efficient transfer of gas from the reservoir (1) to the driver chamber (3) upon actuation. The flow of gas through a restriction such as a bleed-hole creates a loss in energy due to friction meaning that higher initial pressures are required in the reservoir (1) in order to achieve a pressure sufficient to open the closure (4) in the driver chamber (3) if very small bleed-holes are used. Furthermore, a sufficient driver chamber filling rate is required to ensure a repeatable rupture of the membrane, or more generally, a repeatable opening of the closure. If the filling rate is very low, it has been found that the variation in rupture pressure for the same specification membranes is wider than if a higher filling rate is used.

It can be seen therefore that the provision of a bleed-hole along with a silencer having a predetermined effective venting area ensures a useful silencing effect without unduly increasing the pressure inside the device during the operation, thereby avoiding an increased lift-off force which is deleterious to device performance and ease of use. In addition, the subsidiary features of the invention (such as the large silencer volume and small particle exit opening) further reduce the problem of lift-off force without affecting the silencing that can be achieved or the device performance.

The silencing achieved can be such that the use of porous media as was envisaged in WO 94/24263 is not required, thereby reducing the device cost. Nevertheless it may be employed as an alternative or additional restriction method to reduce the noise further.

Figure 2:
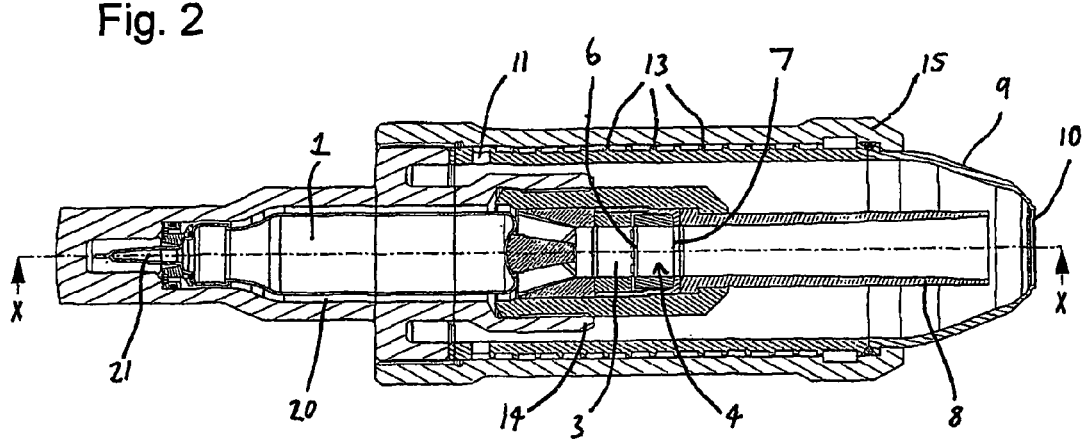
Figure 3:
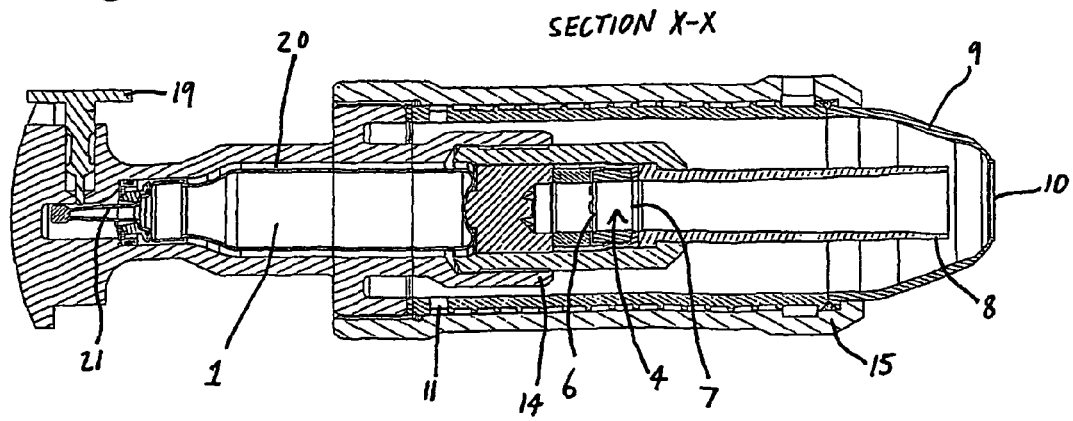

FIGS. 2 and 3 show cross-sections of a practical embodiment of the present invention. The same components as are shown in FIG. 1 are given the same reference numerals. The particles (5) are not shown for clarity, but would (as in FIG. 1) be present in the closure between the rupturable membranes (6, 7)

The gas reservoir (1) has a frangible tip (21) which can be cracked off by application of the button (19). Upon pressing the button gas flows out of the reservoir (1) and into the annular space (20) surrounding the reservoir (1) (see FIGS. 2 and 3). The gas is then directed into the driver chamber (3) which terminates in the closure (4) (see FIG. 2 especially).

The plurality of holes (11) in FIG. 1 are replaced by a single hole in this embodiment and the generally diamond-shaped member (14) of FIG. 1 is replaced by a series of area restrictions in the silencer shroud (9) which are not necessarily diamond shaped. The bleed hole is formed by the smallest area that the gas flows through on its way from the reservoir (1) to the driver chamber (3). In this embodiment, this is formed by the annular space (20) surrounding the gas reservoir (1).

Further, the invention is applicable to the case where "transfer ducts" as disclosed in FIGS. 12a to 12c and 13a to 13c of WO 01/05455 are used to pre-mix (or fluidize) the particles in the particle retention chamber (particle cassette). In this case, there is a further requirement on the size of bleed hole used.

Figure 5:
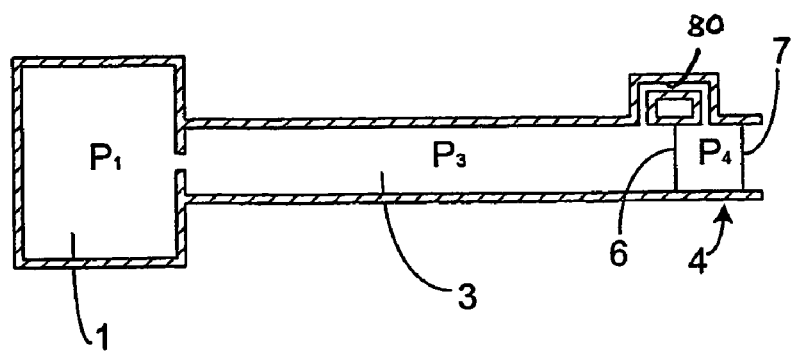

FIG. 5 shows a schematic representation of part of the needleless syringe device as far as the downstream membrane 7. The pressure in the reservoir 1 at any time is referred to as $P_1$, the pressure in the driver chamber is referred to as $P_3$ and the pressure in the particle cassette (between the membranes) is referred to as $P_4$.

To achieve good particle mixing, a gas jet should enter the cassette before either membrane ruptures to thereby mix the particles so they span the entire volume of the cassette. Then, the membranes should burst in sequence with the upstream membrane (6) bursting before the downstream membrane (7). If the downstream membrane (7) bursts first then there is a chance the upstream membrane (6) may never burst, with the gas flow being driven by flow from the reservoir to the driver chamber and through the transfer duct (80).

Figure 6:
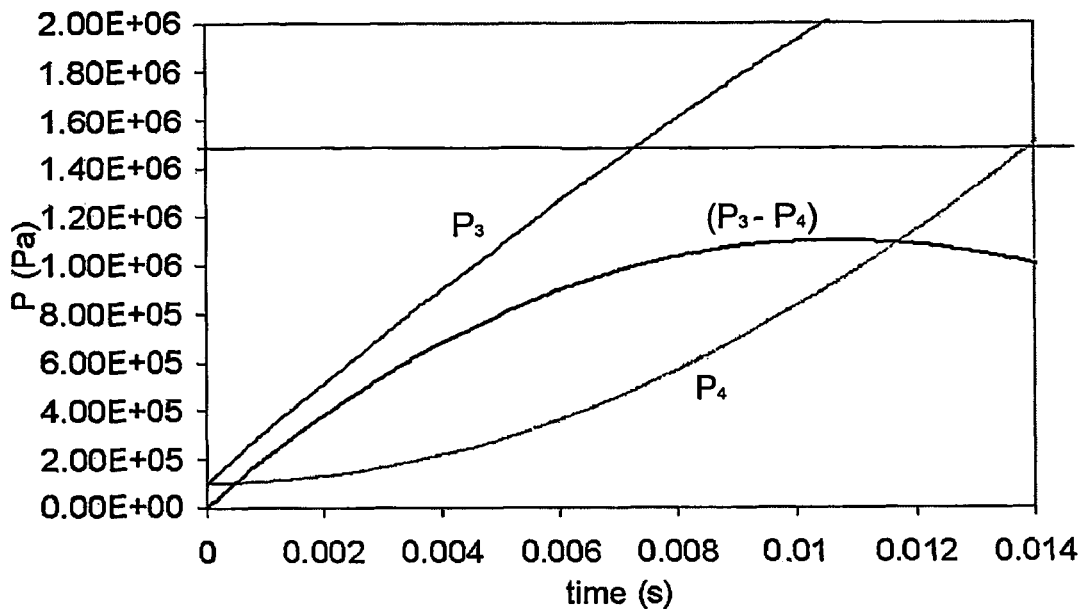

This example is shown in FIG. 6 which is a plot of $P_3$, $P_4$ and ($P_3$-$P_4$) with time. This situation typically results when the bleed hole is too small compared to the area of the transfer duct so that gas pressure in the cassette increases too quickly resulting in the downstream membrane (7) bursting first. The rupture pressure of each membrane is 1.45 MPa and the initial reservoir pressure $P_1$ is 6 MPa. In FIG. 6, it can be seen that the pressure $P_4$ reaches the bursting pressure of 1.45 MPa before the pressure ($P_3$-$P_4$) which is the pressure across the upstream membrane.

Figure 7:
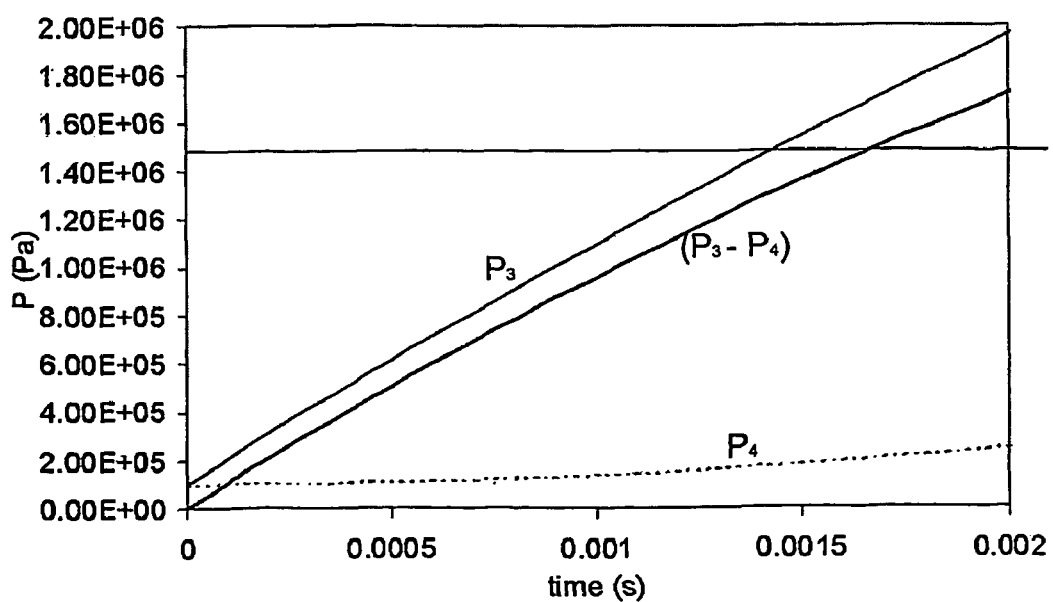

FIG. 7 shows another situation which occurs when the bleed hole is too large in comparison with the transfer duct area. In this case, the pressure $P_3$ increases rapidly and the pressure $P_4$ increases relatively slowly. This results in a rapid successive opening of both membranes in the correct sequence, but with very little particle mixing time (only about 1.65 ms in FIG. 7). This results in limited particle pre-mixing.

Figure 8:
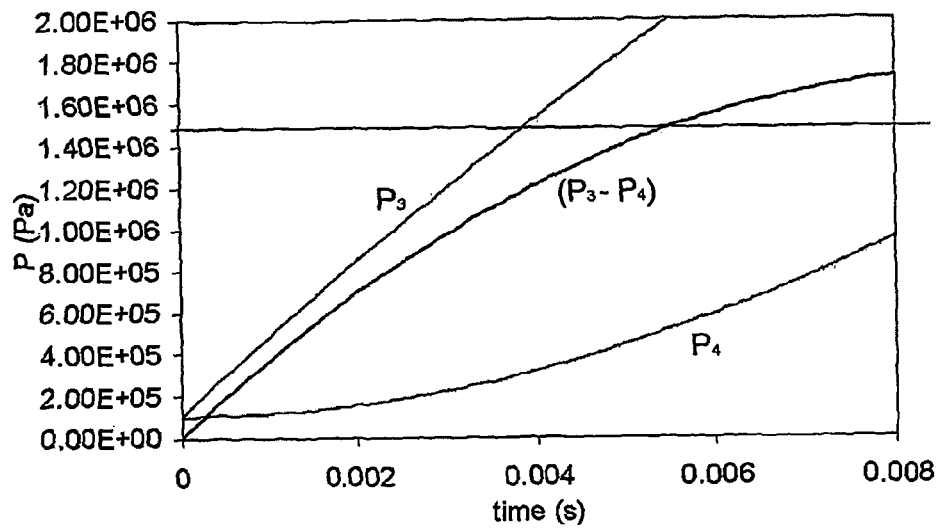

FIG. 8 shows an example where the bleed hole and transfer ports are chosen to have a suitable size. Both membranes rupture in sequence with a mixing time of about 5.5 ms which is adequate to achieve good pre-mixing.

The actual values for the bleed hole and transfer duct sizes depend on the reservoir, driver and cassette volumes, but, once these parameters are selected, the skilled person is able to determine by appropriate simple experiment the correct bleed hole and transfer duct sizes to achieve the results described herein.

The embodiments described have used particle cassettes in which the particles are initially located between two rupturable membranes. However, other mechanisms for locating the particles may be used, not necessarily requiring membranes, for example fast-opening valves. In this regard, reference is made to WO 99/01169 for examples of non-membrane cassettes.

An embodiment of particle cassette ("particle retention assembly") designed to provide pre-mixing and fluidization of the particles, prior to acceleration of the particles will now be described, with reference to FIGS. 9 to 18.

Figure 9:
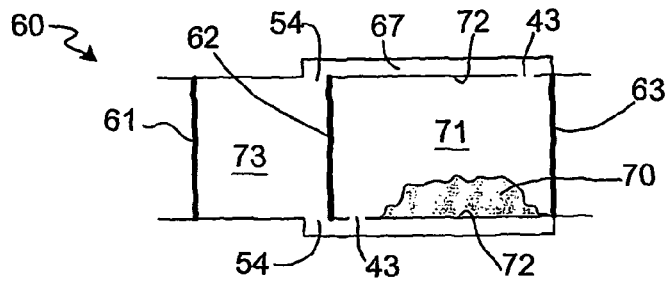

FIG. 9 schematically illustrates a particle retention assembly (60) according to the present invention. The particles (70) are located inside a chamber (71) designed to receive, contain and confine the particles. The inside walls (72) of the chamber (71) are generally cylindrical and in this example there are provided two openings (43) leading to an annular space (67) around the particle retention chamber (71). The particle retention chamber (71) is bounded longitudinally (i.e. at its upstream and downstream ends) by a membrane. The upstream membrane (62) and downstream membrane (63) are designed to rupture when a differential pressure of a certain magnitude is applied across them. The particle retention assembly (60) is sealed at its upstream end by a further rupturable membrane (61). The annular space (67) is fluidly connected to the region upstream of the upstream rupturable membrane (62) by circumferential ports (54). The region (73) upstream of the membrane (62) is also generally cylindrical in configuration and has a diameter substantially equal to the diameter of the particle retention chamber (71).

Figure 10A:
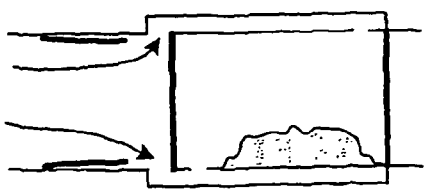
Figure 10B:
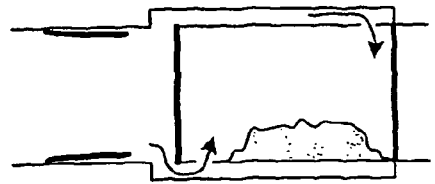
Figure 10C:
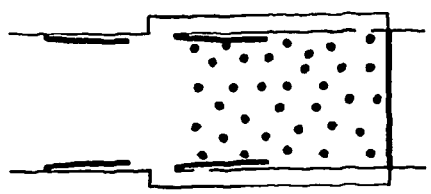
Figure 10D:
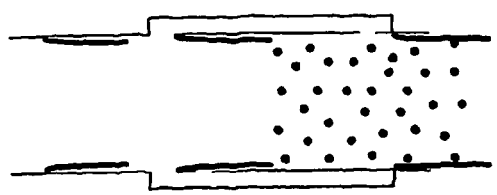
Figure 11:
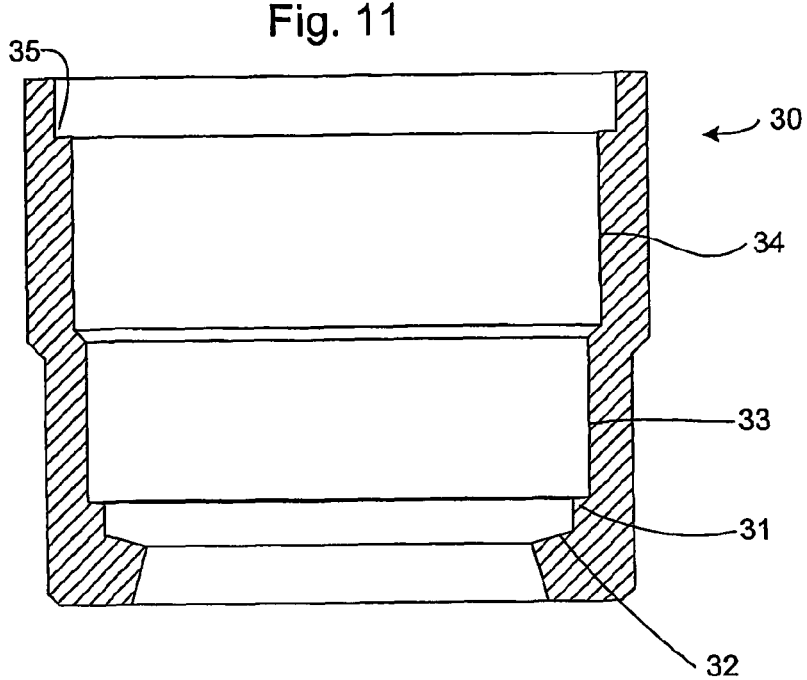
Figure 12:
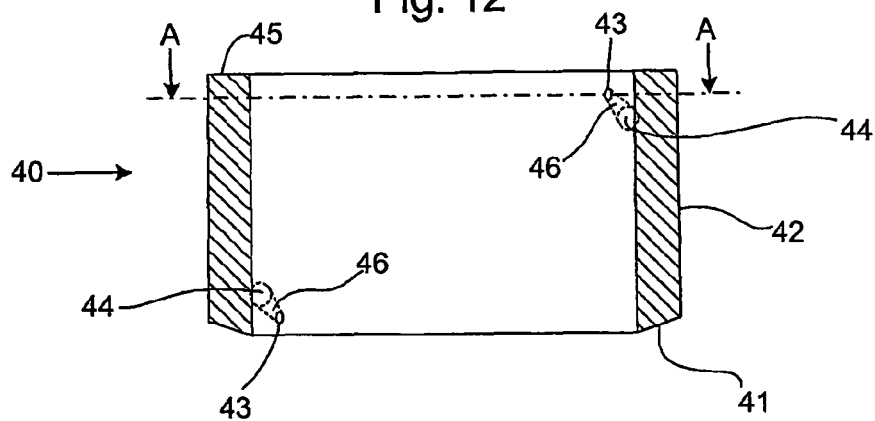

FIGS. 10a to 10b illustrate the working of the particle retention assembly. In use, the particle retention assembly (60) is used as a particle cassette (4) for the needleless syringe shown in FIG. 1. Thus, the membrane (61) is presented with the gas pressure from the driver chamber 3 and the downstream membrane (63) prevents the particles (70) (referenced (5) in FIG. 1) from falling out of the nozzle, through the exit plane (10) and out of the device.

On actuation, gas is allowed to flow through the bleed-hole (2) from the reservoir (1) so that the pressure in the driver chamber (5) increases. When the pressure in the driver chamber (3) increases to a magnitude larger than the pressure in the chamber (73) by a predetermined amount, the membrane (61) ruptures. For most applications it is envisaged that the initial pressure in the chamber (73) (and thus in the chamber (71)) will be atmospheric pressure (approximately 100 kPa). When the membrane (61) ruptures (e.g. at a differential pressure of 600 kPa), that is to say a pressure downstream of the membrane (61) of 100 kPa and a pressure upstream of the membrane (61) of 700 kPa), gas flows into the chamber (73) and impinges on the membrane (62) (see FIG. 10*a*). The membrane (62) is designed to rupture at a higher differential pressure (e.g. 1.45 MPa) than the membrane (61). Thus, gas continues to flow through the bleed-hole (2) and the pressure in chamber (73) increases. Gas flows through the vent holes (54) and into the annular space (67) surrounding the particle retention chamber (71). From there, the gas flows through the openings (43) and into the chamber (71) (see FIG. 10*b*). The openings (43) are shaped and directed such that the gas forms jets, preferably sonic or supersonic jets which create gas swirls (Vortices) inside the particle retention chamber (71). These gas flows entrain the particles (70) and cause them to become fluidized in the gas such that the particles no longer are clumped together but span the whole volume of the particle retention chamber (71). The pressure in the driver chamber continues to increase until the upstream membrane (62) ruptures. The result of this is shown in FIG. 10*c*. As can be seen, the particles are well fluidized in the cassette due to the pre-mixing provided by the gas jets shown in FIG. 10*b*.

Since the volume of particle retention chamber (71) is generally fairly small, it does not take long before the pressure upstream of membrane (63) is such as to cause bursting of that membrane, as shown in FIG. 10*d*. From thenceforth, the flow previously described in which the particles are accelerated out of the particle retention assembly (60) and through the nozzle (8) into the target is established. Since the particles are not lumped together (as shown in FIG. 9) when the upstream membrane (62) ruptures, it has been found that a more even spread of particles and therefore a more homogonous particle distribution is obtained. Similarly, a more homogonous velocity distribution is also obtained. This results in the particles being evenly distributed across the target and penetrating to depths that are within the defined tolerances.

One preferred physical construction of the particle retention assembly (60) will now be described. It should be appreciated that this is a preferred construction only and that it may be modified in various ways to achieve the desired result. For example, it is not necessary that there are two transfer ducts (46) leading to two openings (43) and satisfactory operation has been obtained when there is only one opening (43). Furthermore, the openings (43) are not limited to being adjacent the membrane (62) or (63) and can in general be located anywhere along the inside wall (72) of the particle retention chamber (71). Moreover, the cylindrical inside walls and circumferential ports are merely preferred and any shape that achieves the function may be used.

FIGS. 11 and 12 show in cross-sectional view second and first cassette parts respectively. The second cassette part (30) of FIG. 11 is generally cylindrical in configuration having substantially vertical inside walls (33) and (34). The inside wall (33) has a slightly smaller diameter than inside wall (34) for reasons that will become apparent later. A shoulder portion (31) is provided adjacent a seating face (32). The shoulder portion (31) is designed to interact with the external surface of the first cassette part (40), described hereafter. A recess (35) is provided at the top end of the second cassette part (30) and this recess (35) aids in assembling the cassette.

FIG. 12 shows a first cassette part (40) according to the present invention. The first cassette part (40) comprises a substantially annular member defining within its confines a receptacle (or chamber) for receiving particles. The first cassette part (40) has generally cylindrical outer walls (42) and a slightly tapered seating face (41) at its bottom end. The seating face (41) is intended to rest against the seating face (32) of the second cassette part (30) during use. Furthermore, the shoulder (31) of the second cassette part (30) is intended to abut the outer surface (42) of the first cassette part to provide an interference fit. This configuration is shown in FIG. 15.

Referring back to FIGS. 12 and 13, there are openings (43) on the inner surface of the first cassette part (40) and openings (44) on the outer surface of the first cassette part (40). These openings are connected by transfer ducts (46) such that gas surrounding the first cassette part (40) may enter the receptacle for receiving particles. The transfer ducts (46) are substantially conical in shape converging inwardly. They are angled in three dimensions such that when gas flows therethrough a preferably sonic or supersonic jet is formed which tends to create a swirling gas movement inside the chamber confining the particles. The transfer ducts (46) are angled such that the gas tends to impinge against the membranes (62,63) located at either side of the first cassette part (40). Furthermore, the openings (43) are provided at different longitudinal ends of the first cassette part (40) and are directed in different directions such that a clockwise gas flow is established at one end of the particle confinement chamber and an anti-clockwise gas flow is established at the other end of the particle confinement chamber. This is illustrated in FIG. 16 wherein the gas flows are referenced (65) and (66). As is clear from FIG. 13, the transfer ducts (46) are provided on the same lateral side of the first cassette part (i.e. above the centre line shown in FIG. 13), and this has been found to provide for good fluidization of the particles when gas pressure is introduced to the openings (44) and a flow of gas is established through the transfer ducts (46). However, other configurations of transfer duct in the side walls of the first particle cassette part (40) can provide good results and it is not generally essential for the present invention that the transfer ducts (46) have the specific form shown in FIGS. 12 and 13.

FIGS. 12 and 13 show an advantageous configuration of transfer ducts (46) wherein the ducts are offset from one another both in the direction of gas flow and also circumferentially. The longitudinal (i.e. in the direction of gas flow) offset is shown in FIG. 12 as being substantially equal to the longitudinal length of the particle retention chamber although this is not essential and a lesser degree of off-set may be used. The transfer ducts are also angled to direct gas outwardly against the membranes (62,63). The interaction of the jets emitted by the openings (43) with the membranes and the resulting swirls of gas have been found to cause effective particle mixing.

Figure 13:
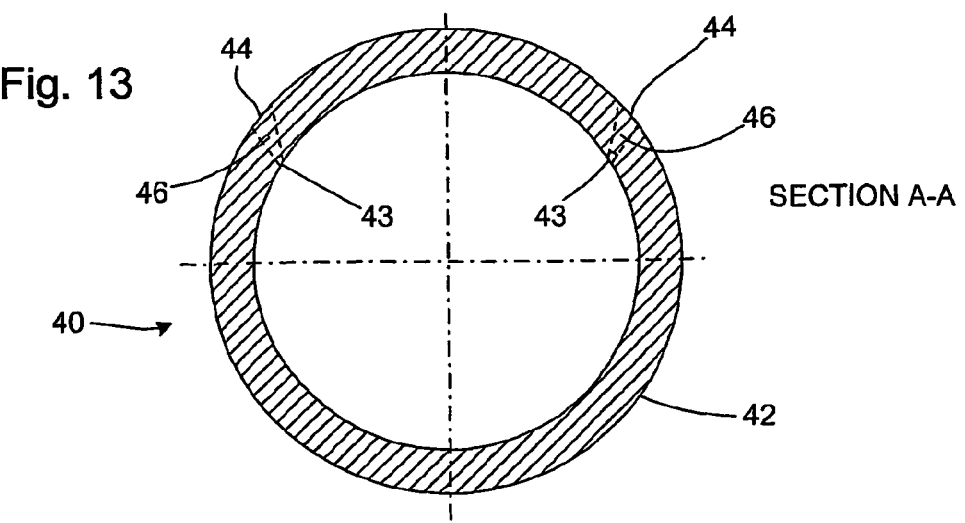

As is clear from FIG. 13, the transfer ducts (46) are angled so as to create swirls of gas which rotate in opposite directions. The right-hand transfer duct (46) of FIG. 13 is adapted to create a substantially clockwise swirl of gas in the particle retention chamber and the left-hand transfer duct (46) of FIG. 13 is adapted to create a substantially anti-clockwise swirl of gas in the particle retention chamber (71). In FIG. 13, the openings (43) are circumferentially offset by an angle of about 120° and it is preferable that any circumferential offset falls in the range of from 90° to 180° inclusive. Other circumferential off-sets may be used, however.

Figure 14:
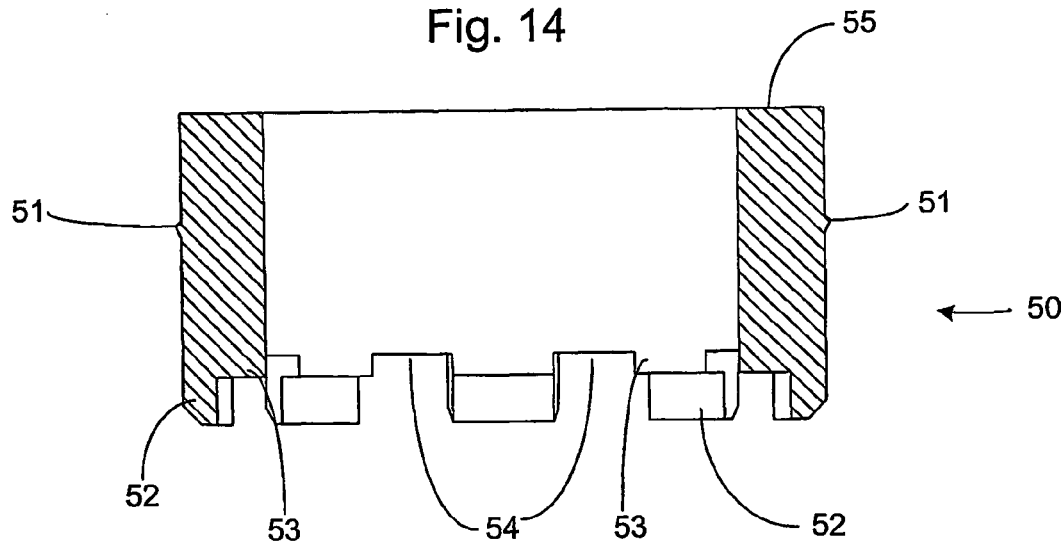

FIG. 14 shows a third particle cassette part in accordance with the present invention.

Figure 15:
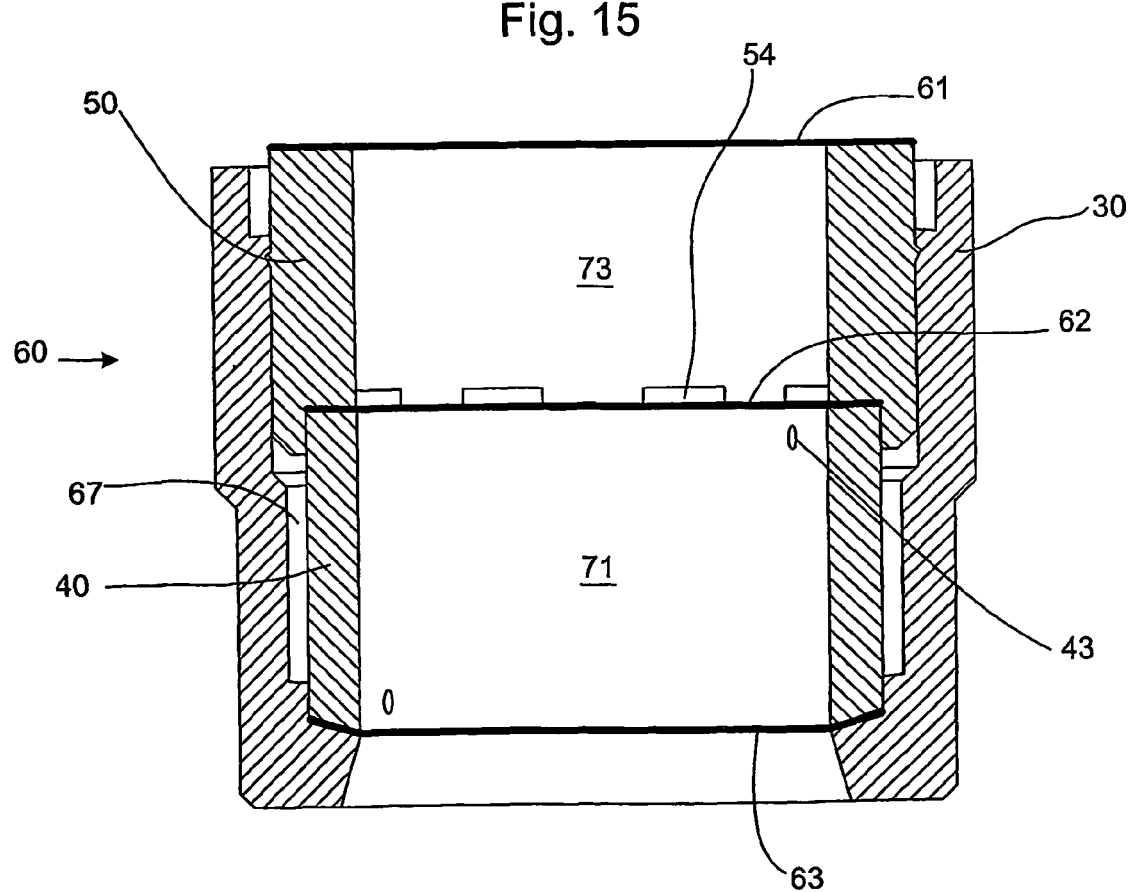

The third cassette part (50), in common with the first and second cassette parts, has generally cylindrical inner and outer walls forming an annular-shaped member. One or more protrusions (51) may be formed on the outer walls and these are intended to provide an interference fit against the inner wall (34) of the second cassette part (30), when the particle cassette is assembled. The lower end of the third cassette part (50) has a number of formations (52) around the circumference. The formations (52) are stepped and are designed such that the top part (53) of the formations (52) abuts the top surface of the first cassette part (40) when assembled, as shown in FIG. 15. The formations are spaced apart by vent holes (54) that are formed such that gas may pass through the vent holes (54) when the first and third cassette parts are attached together. The formations (52) are shaped so as to grip, by means of friction, or interference, the top part of the first cassette part (40).

The particle cassette takes the form shown in FIG. 15 when assembled. In this embodiment the membrane (61) is relatively thin with a fairly low bursting pressure and is designed to keep the unit sterile in use. If it were not for this there is a chance that particles could travel through the openings (43), into the annular space (67), through the vents (54) and out through the upstream end of the particle retention assembly.

To assemble the particle cassette, a first membrane (62) is heat sealed or bonded to the upper edge of the first cassette part (40). Similarly, the second membrane (63) is heat sealed or bonded to the seating face (32) of the second cassette part (30). The third membrane (61) is heat sealed or bonded to the upper face of the third cassette part (50). The first membrane and first cassette part thus define a receptacle in which the particles may be contained. The openings (43) are very small such that it is very difficult for the particles to pass out of the chamber once inside. Once the particles have been supplied to the chamber of the first cassette part (40), the first cassette part (40) is brought together with the second cassette part (30) with the leading edge of the first cassette part engaging the shoulders (31) of the second cassette part. The first cassette part (40) is pushed in until the seating face (41) of the first cassette part abuts the seating face (32) of the second cassette part (with the second membrane (63) between the two seating faces). In this configuration, the particles are trapped between the first and second membranes. The third cassette part (50) having the third membrane (61) thereon is then pushed in so that the formations (52) slide into the annular gap created between the first and second cassette parts. Interference and/or friction ensure that this movement firmly secures the first and second parts together and effectively "locks" the cassette. It will be appreciated that it is quite difficult to remove the third cassette part once it is installed, especially if the top face (55) of the third cassette part is dimensioned so as to be flush with the top face of the second cassette part when assembled (this is not shown in FIG. 15 however).

The membrane (61) ensures that the particles inside the cassette may not come into contact with any external particles or gases and thus the membrane (61) ensures the sterility of the cassette.

In use, the cassette is inserted into a needleless syringe such as that shown in FIGS. 2 and 3 and gas pressure is supplied to the third membrane (61). The membrane (61) bursts quite easily and gas enters the internal space (73) defined by the third cassette part. Gas is able to flow through the vents (54) and into the annular space (67) between the first cassette part and the second cassette part. From there, gas may pass through the transfer ducts (46) and out through the openings (43) into the particle containment chamber. The jets of gas so formed cause the particles to be fluidized and mixed.

Figure 16:
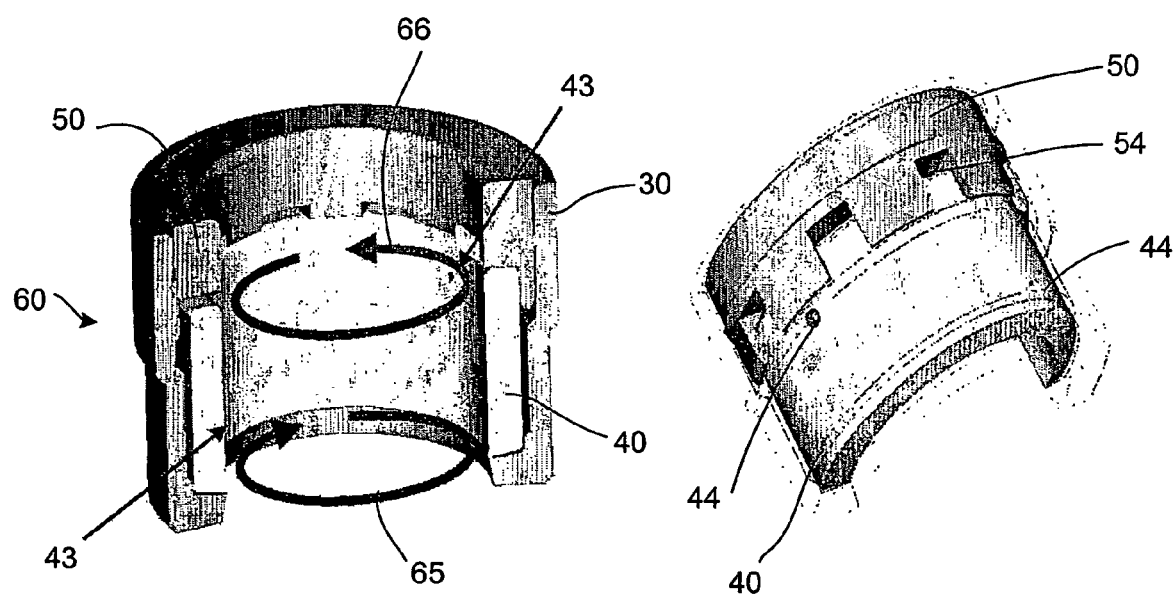

FIG. 16 shows the swirls (65,66) of gas that are set up within the particle retention chamber (71) in use (the membranes are not shown in FIG. 16 for clarity).

Following such fluidizing, the upstream membrane (62) bursts and the particles are entrained in the bulk of the gas flow followed by the bursting of the downstream membrane (63) shortly thereafter.

Heat sealing or adhesive is not necessary to seal the membranes and the first and second membranes may be sealed against the first and second cassette parts respectively due to the tight fit between the various cassette parts. For example, the first membrane (62) may be sealed by virtue of being trapped between the first and third cassette parts. Similarly, the second membrane (63) may be trapped between the first and second cassette parts, with no special heat sealing or adhesive step being required.

Figure 17:
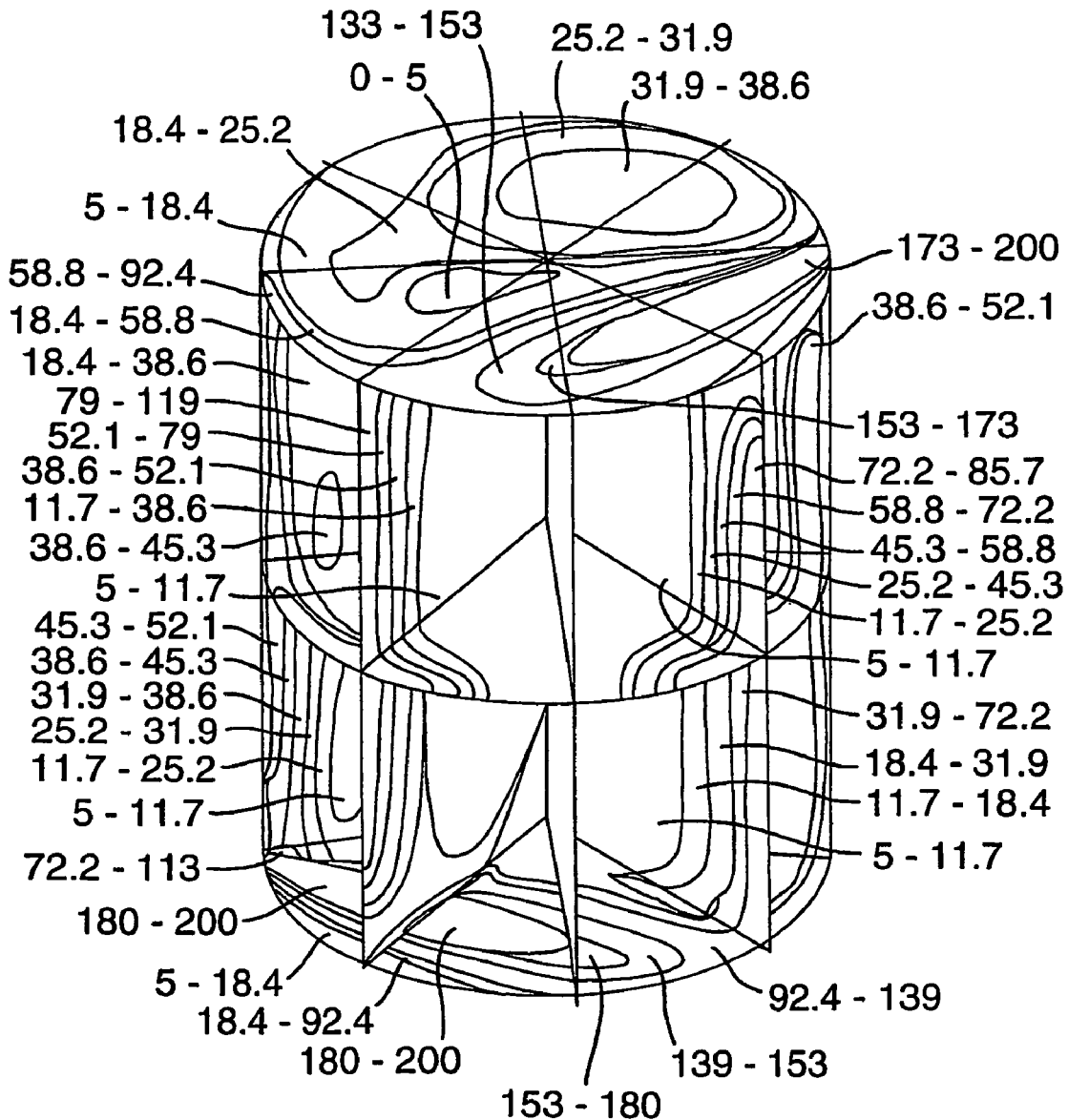
Figure 18:
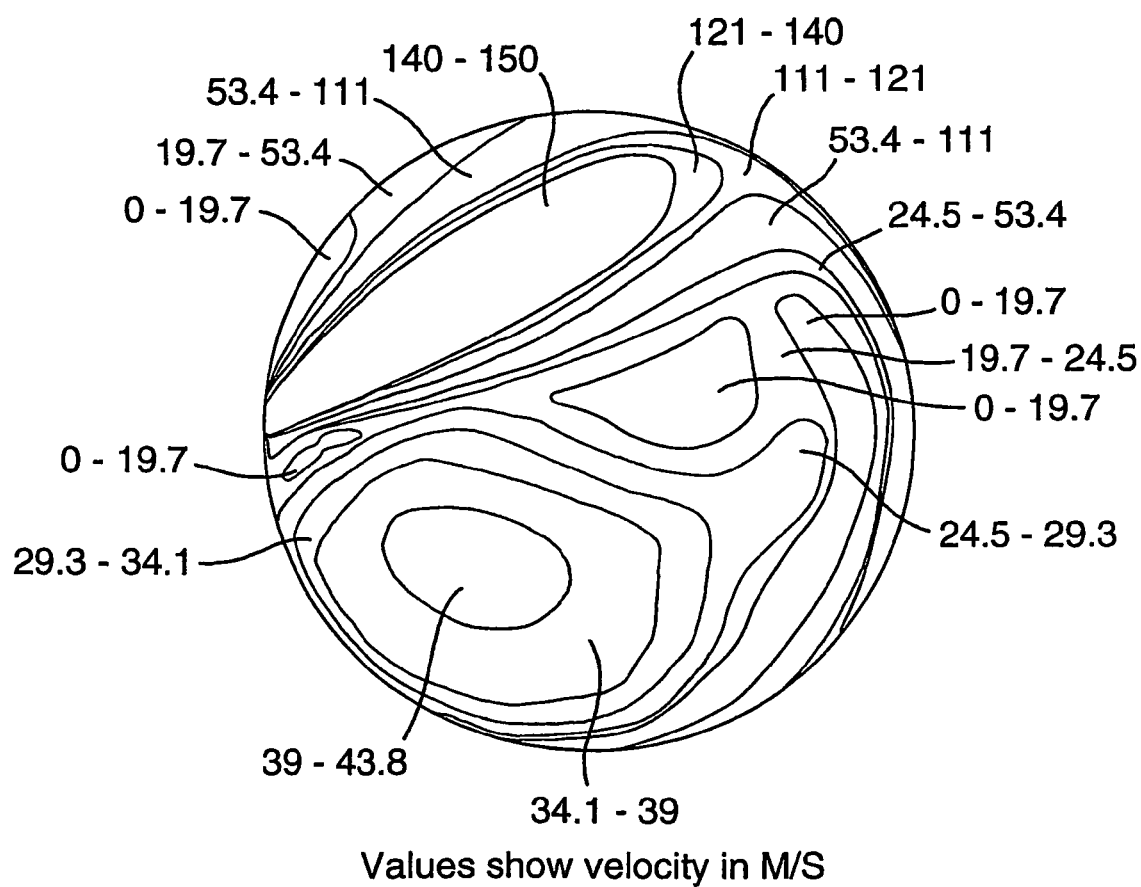

FIGS. 17 and 18 show the result of a computational fluid dynamic analysis of the flow inside the particle retention assembly.

FIG. 17 shows a model of the particle retention chamber (71) with the membranes at the top and bottom. The jet emitted by the openings (43) has a velocity in the region of 200 m/s. Since the jet is directed into the wall of the particle retention chamber (71), and the wall is substantially cylindrical, the flow is directed around the wall, creating a swirling motion. Some of the flow is also directed in a longitudinal direction towards the centre of the chamber. It can be seen that the two jets cause swirls to form in opposite directions and that the main downward flow from the top jet impinges downwardly on the bottom jet. Likewise, due to symmetry, the main upward flow arising from the bottom jet impinges centrally into the top jet. Thus, particles entrained by one jet are fed into the other, creating a circulating motion of particles in the chamber. This causes good fluidisation of particles.

FIG. 18 shows the jet in more detail. The flow slows down as it hits the wall of the chamber and is deflected in three dimensions around the circumference and downwardly into the plane of the page. The velocity of the jet is approximately 150 m/s.

For each of the embodiments, the materials used to manufacture the cassette parts and the membranes may be conventional, for example, the membranes may be mylar as disclosed in WO 94/24263 and the first and second cassette parts are preferably manufactured from a plastics material, using injection moulding for example. Both the membranes and cassette parts may be made from polycarbonate such as Evaxone 260 (EVA) polymer. If heat sealing is used, a temperature of 110° C. and pressure of 760 kPa (110 psi) for 1.5 seconds has been found to be acceptable.

The cassette is suitable for any type of particle, including powdered drugs and carrier particles coated in genetic material.

The invention claimed is:

1. A needleless syringe device comprising:
   an energy source;
   at least one bleed-hole, said bleed-hole(s) having an effective bleed-hole area for the passage therethrough of pressurized gas from the energy source to a driver chamber to entrain particles and accelerate them into a target; and
   a silencer for receiving said gas from said driver chamber and for venting that gas to the surroundings of the silencer through at least one silencer vent opening, said vent opening(s) having an effective venting area;
   wherein said effective bleed-hole area and said effective venting area are such that, during use of the device for particle delivery, the mass flow rate of gas through said effective venting area is substantially equal to or greater than the mass flow rate of gas through said effective bleed-hole area.

2. A needleless syringe device according to claim 1, wherein said energy source is a reservoir of pressurized gas.

3. A needleless syringe device according to claim 2, wherein said effective bleed-hole area and said effective venting area are such that:

$$\left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S} \leq$$

$$\frac{\text{venting area}}{\text{bleed-hole area}} \leq 10 \left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S}$$

wherein $\gamma_1$ is the ratio of specific heats for the gas in the reservoir, $R_1$ is the gas constant for the gas in the reservoir, $\gamma_2$ is the ratio of specific heats for the gas in the surroundings, $R_2$ is the gas constant for the gas in the surroundings, $P_0$ is the pressure in the energy source after gas has been received by said silencer and $P_S$ is the pressure in the silencer after gas has been received by said silencer.

4. A needleless syringe device according to claim 3, wherein said effective bleed-hole area and said effective venting area are such that:

$$1.2 \left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S} \leq \frac{\text{venting area}}{\text{bleed-hole area}}.$$

5. A needleless syringe device according to claim 4, wherein said effective bleed-hole area and said effective venting area are such that:

$$\frac{\text{venting area}}{\text{bleed-hole area}} \leq 5 \left( \frac{(\gamma_1/R_1)\left(1 - \frac{\gamma_1 - 1}{2}\right)^{\gamma_1 - \frac{1}{2}}}{(\gamma_2/R_2)\left(1 - \frac{\gamma_2 - 1}{2}\right)^{\gamma_2 - \frac{1}{2}}} \right) \frac{P_0}{P_S}.$$

6. A needleless syringe device according to claim 1, wherein said silencer comprises:
   a shroud having a predetermined volume for containing said gas received from said driver chamber prior to venting it.

7. A needleless syringe device according to claim 6, wherein said shroud comprises:
   a particle exit opening to be pressed against said target during use so that said particles may pass through said opening and into said target.

8. A needleless syringe device according to claim 7, wherein the silencer shroud and driver chamber each have a respective volume, and wherein said particle exit opening has an area such that a lift off force on the device during use is less than 20N.

9. A needleless syringe device according to claim 7, wherein the silencer shroud and driver chamber each have a respective volume, and wherein said particle exit opening has an area such that a lift off force on the device during use is less than 15N.

10. A needleless syringe device according to claim 6, wherein said shroud has a volume greater than that of said driver chamber by at least 5 times.

11. A needleless syringe device according to claim 6, wherein said shroud comprises:
    elements which restrict the cross-sectional area of the shroud to attenuate shockwaves that pass along said shroud.

12. A needleless syringe device according to claim 6, wherein said shroud is provided with at least one hole forming said at least one silencer vent opening.

13. A needleless syringe device according to claim 12, wherein said at least one hole is/are located substantially in an upstream end of the device.

14. A needleless syringe device according to claim 6, further comprising:
    a cover to create an annular channel for the passage of gas from said shroud to the surroundings.

15. A needleless syringe device according to claim 14, further comprising:
    a plurality of baffles in said annular channel to interact with the gas flow out of said shroud.

16. A needleless syringe device according to claim 1, further comprising:
    a resistive material to breakdown a shockwave travelling through said device.

17. A needleless syringe device according to claim 7, further comprising:
    a nozzle connected to said driver chamber for expanding the particle-containing gas which flows from said driver chamber.

18. A needleless syringe device according to claim 17, wherein said particle exit opening is no more than 100% larger than the exit area of said nozzle and said opening is axially spaced from said nozzle exit.

19. A needleless syringe device according claim 1, further comprising:
    a first and second membrane at a downstream end of the driver chamber, said first and second membranes being spaced apart longitudinally so as to create a particle retention chamber.

20. A needleless syringe device according to claim 19, further comprising:
a transfer duct for supplying pressurized gas from said driver chamber to said particle retention chamber.

21. A needleless syringe device according to claim 20, wherein said bleed-hole area and the minimum area of said transfer duct are selected such that, in use, an upstream one of said membranes bursts before a downstream one of said membranes.

22. A needleless syringe device according to claim 21, wherein, in use, said downstream membrane bursts more than 2 ms after gas starts to flow through said transfer duct.

23. A needleless syringe device comprising:
an energy source;
at least one bleed-hole, said bleed-hole(s) having an effective bleed-hole area for the passage therethrough of pressurized gas from the energy source to a driver chamber;
a first closure located at a downstream end of said driver chamber;
a second closure located downstream of said first closure to create a particle retention chamber therebetween; and
at least one transfer duct providing a gas flow path between said driver chamber and said particle retention chamber;
wherein said effective bleed-hole area and the minimum area of said transfer duct(s) are selected such that, in use, said first closure opens before said second closure, and wherein said second closure opens at least 2 ms after gas starts to flow through said transfer duct(s).

24. A needleless syringe device according to claim 23, wherein said first and second closures are rupturable membranes which open by rupturing.

25. A needleless syringe device according to claim 23, wherein said second closure opens at least 3.5 ms after gas starts to flow through said transfer duct(s).

26. A needleless syringe device according to claim 23, wherein said second closure opens at least 5 ms after gas starts to flow through said transfer duct(s).

27. A needleless syringe device according to claim 6, wherein said shroud has a volume greater than that of said driver chamber by at least 10 times.

28. A needleless syringe device according to claim 6, wherein said shroud has a volume greater than that of said driver chamber by at least 20 times.

29. A needleless syringe device according to claim 23, wherein said device includes a flow path directly between said driver chamber and said particle retention chamber, and an additional flow path from said driver chamber to said particle retention chamber via said transfer duct(s).

* * * * *